(12) United States Patent
Marek

(10) Patent No.: US 10,656,050 B2
(45) Date of Patent: May 19, 2020

(54) SYSTEM AND METHOD FOR DETECTING A LEAK IN AN EXHAUST GAS SAMPLING APPARATUS

(71) Applicant: AVL TEST SYSTEMS, INC., Plymouth, MI (US)

(72) Inventor: Gerald Marek, Pinckney, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 143 days.

(21) Appl. No.: 15/638,666

(22) PCT Filed: Jan. 8, 2016

(86) PCT No.: PCT/US2016/012618
§ 371 (c)(1),
(2) Date: Jun. 30, 2017

(87) PCT Pub. No.: WO2016/112269
PCT Pub. Date: Jul. 14, 2016

(65) Prior Publication Data
US 2018/0195927 A1    Jul. 12, 2018

Related U.S. Application Data

(60) Provisional application No. 62/101,629, filed on Jan. 9, 2015.

(51) Int. Cl.
*G01M 15/02* (2006.01)
*G01N 1/22* (2006.01)
(Continued)

(52) U.S. Cl.
CPC .............. *G01M 15/02* (2013.01); *G01M 3/28* (2013.01); *G01N 1/2252* (2013.01);
(Continued)

(58) Field of Classification Search
CPC ........ G01M 3/28; G01M 3/26; G01M 3/2807; G01M 15/02; G01M 15/04; G01M 15/06;
(Continued)

(56) References Cited

U.S. PATENT DOCUMENTS 3,565,252 A * 2/1971 Sheehy ................. B01D 17/02
210/104
5,243,847 A    9/1993 Engeljehringer et al.
(Continued)

FOREIGN PATENT DOCUMENTS

JP    H09-061283 A    3/1997
JP    H10-185819 A    7/1998
(Continued)

OTHER PUBLICATIONS

Translation of First Office Action dated Oct. 29, 2019 corresponding to Japanese Patent Application No. 2017-555426, 7 pages.
(Continued)

*Primary Examiner* — Justin N Olamit
(74) *Attorney, Agent, or Firm* — Harness, Dickey & Pierce, P.L.C.

(57) ABSTRACT

An exhaust gas sampling system according to the principles of the present disclosure includes a dilution air source that provides dilution air to a first flow path and a first flow meter that measures a first mass flow rate in the first flow path. The system further includes a sampling probe, a second flow meter, a first valve, and a leak detection module. The sampling probe provides exhaust gas to the first flow path at a location downstream from the first flow meter. The second flow meter measures a second mass flow rate in the first flow path at a location downstream from the sampling probe. The first valve regulates exhaust gas flow from the sampling probe to the second flow meter. The leak detection module detects a leak in the system based on measurements of the
(Continued)

first and second mass flow rates taken when the first valve is closed.

16 Claims, 5 Drawing Sheets

(51) Int. Cl.
 *G01M 3/28* (2006.01)
 *G01N 33/00* (2006.01)
 *G01M 15/10* (2006.01)

(52) U.S. Cl.
 CPC ....... *G01N 33/0006* (2013.01); *G01M 15/102* (2013.01); *G01N 1/2211* (2013.01); *G01N 2001/2255* (2013.01); *G01N 2001/2264* (2013.01)

(58) Field of Classification Search
 CPC .... G01M 15/08; G01M 15/10; G01M 15/102; G01M 15/104; G01M 15/106; G01M 15/108; G01M 15/11; G01N 1/2252; G01N 2001/2255; G01N 2001/2264
 See application file for complete search history.

(56) References Cited

U.S. PATENT DOCUMENTS

| | | | |
|---|---|---|---|
| 5,546,788 | A | 8/1996 | Dickow |
| 6,370,936 | B1* | 4/2002 | Yamagishi .......... G01F 25/0053 73/1.35 |
| 6,481,265 | B1* | 11/2002 | Weber .................. G01M 3/28 73/40 |
| 6,615,677 | B2 | 9/2003 | Dickson et al. |
| 6,729,195 | B2 | 5/2004 | Graze, Jr. |
| 6,993,428 | B1 | 1/2006 | Gundrum |
| 7,243,559 | B2 | 7/2007 | Dickson et al. |
| 7,281,440 | B2* | 10/2007 | Graze, Jr. .......... G01M 15/102 73/114.42 |
| 7,299,690 | B2 | 11/2007 | Graze, Jr. |
| 7,404,340 | B2 | 7/2008 | Dickson et al. |
| 7,406,885 | B2 | 8/2008 | Graze, Jr. |
| 7,533,585 | B2 | 5/2009 | Graze, Jr. |
| 7,549,350 | B2 | 6/2009 | Graze, Jr. |
| 7,565,846 | B2 | 7/2009 | Silvis et al. |
| 7,574,307 | B2* | 8/2009 | Silvis ................. G01F 25/0053 702/30 |
| 7,607,335 | B2 | 10/2009 | Marek et al. |
| 8,505,395 | B2* | 8/2013 | Graze, Jr. ............ G01N 1/2202 73/863.51 |
| 9,074,512 | B2* | 7/2015 | Asami .................... F01N 11/00 |
| 9,869,220 | B2* | 1/2018 | Abdul-Khalek ......... F01N 3/02 |
| 2006/0243026 | A1 | 11/2006 | Graze et al. |
| 2008/0148812 | A1 | 6/2008 | Wei et al. |
| 2009/0265074 | A1 | 10/2009 | Heinrich et al. |
| 2010/0058878 | A1 | 3/2010 | Samaras et al. |
| 2012/0017666 | A1 | 1/2012 | Otsuki et al. |
| 2014/0019077 | A1 | 1/2014 | Berghof |
| 2014/0338426 | A1 | 11/2014 | Noda et al. |

FOREIGN PATENT DOCUMENTS

| | | |
|---|---|---|
| JP | 2006-084263 A | 3/2006 |
| JP | 2010-515017 A | 5/2010 |
| JP | 2012-026892 A | 2/2012 |
| JP | 2013-503340 A | 1/2013 |
| WO | WO-2013188346 A1 | 12/2013 |

OTHER PUBLICATIONS

International Search Report for PCT Application No. PCT/US2016/012618 dated Apr. 16, 2016; 3 pages.

Engeljehringer, K. et al. SAE Technical Paper Series: 932466. "Meeting ISO 8178 Requirements for the Measurement of Diesel Particulates with Partial-Flow Dilution Systems". 1993 International Off-Highway & Powerplant Congress & Exposition; Milwaukee, Wisconsin; Sep. 13-15, 1993; 12 pages.

International Standard ISO; Reference Number: ISO 16183:2002(E). "Heavy-duty engines—Measurement of gaseous emissions from raw exhaust gas and of particulate emissions using partial flow dilution systems under transient test conditions". First edition: Dec. 15, 2002; 72 pages.

\* cited by examiner

SYSTEM AND METHOD FOR DETECTING A LEAK IN AN EXHAUST GAS SAMPLING APPARATUS

CROSS-REFERENCE TO RELATED APPLICATIONS

This application is a National Stage of International Application No. PCT/US2016/012618, filed on Jan. 8, 2016, which claims the benefit of U.S. Provisional Application No. 62/101,629, filed on Jan. 9, 2015. The entire disclosure of each of the applications referenced above is incorporated herein by reference.

FIELD

The present disclosure relates to exhaust gas sampling systems and, more particularly, to systems and methods for detecting leaks in an exhaust gas sampling apparatus.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

An exhaust gas sampling apparatus typically includes a dilution air supply passage that provides dilution air to a dilution air tunnel, and a sampling probe that provides exhaust gas to the dilution air tunnel. The dilution air may be clean, filtered air that is free of oil, such as zero air or nitrogen, and may be compressed air. In the dilution air tunnel, particles in the exhaust gas react with the dilution air, causing the particles to experience condensational growth. This growth of the emissions particles improves the accuracy of emissions analyzers in the exhaust gas sampling systems.

On occasion, an exhaust gas sampling apparatus may develop a leak due to, for example, improper assembly, a defect in a component, or wear. Conventional systems and methods for detecting a leak in an exhaust gas sampling apparatus either pressurize the apparatus or create a vacuum in the apparatus and monitor the pressure in the apparatus. If a change in the pressure is greater than a predetermined amount within a predetermined period, the systems and methods detect a leak in the exhaust gas sampling apparatus. These conventional systems and methods may not detect a leak in an exhaust gas sampling apparatus as accurately and/or as quickly as desired.

SUMMARY

A first example of an exhaust gas sampling system according to the principles of the present disclosure includes a dilution air source, a first flow meter, a sampling probe, a first valve, and a leak detection module. The dilution air source provides dilution air to a first flow path. The first flow meter measures a first mass flow rate of air in the first flow path. The sampling probe has an outlet disposed in the first flow path downstream from the first flow meter and provides exhaust gas to the first flow path. The second flow meter measures a second mass flow rate of air in the first flow path downstream from the sampling probe. The first valve allows exhaust gas flow from the sampling probe to the second flow meter when the first valve is open and prevents exhaust gas flow from the sampling probe to the second flow meter when the first valve is closed. The leak detection module detects a leak in the exhaust gas sampling system based on measurements of the first mass flow rate and the second mass flow rate taken when the first valve is closed.

In one aspect, the leak detection module detects a leak in the exhaust system based on a difference between the first mass flow rate and the second mass flow rate. In another aspect, the leak detection module detects a leak in the exhaust system when the difference between the first mass flow rate and the second mass flow rate is greater than a predetermined value. In another aspect, the first valve is disposed in the sampling probe. In yet another aspect, the first valve is disposed in the first flow path downstream from the outlet of the sampling probe.

In other aspects, the exhaust gas sampling system further includes a second flow path and a valve assembly. The second flow path extends from a first location in the first flow path to a second location in the first flow path. The first location is downstream from the first flow meter and upstream from the outlet of the sampling probe. The second location is downstream from the outlet of the sampling probe and upstream from the second flow meter. When the valve assembly is in a first position, the valve assembly allows air flow through the first flow path to the outlet of the sampling probe and prevents air flow through the second flow path from the first location to the second location. When the valve assembly is in a second position, the valve assembly prevents air flow through the first flow path to the outlet of the sampling probe and allows air flow through the second flow path from the first location to the second location.

In another aspect, the valve assembly includes a second valve and a third valve. The second valve is disposed in the first flow path downstream from the first location and upstream from the outlet of the sampling probe. The third valve is disposed in the second flow path downstream from the first location and upstream from the second location.

In another aspect, the exhaust gas sampling system further includes an add on sampling (AOS) device that detects properties of particles in exhaust gas flowing through the first flow path and that allows gas to escape the first flow path. The AOS device has an inlet in communication with the first flow path at a first location that is downstream from the outlet of the sampling probe. The AOS device has an outlet in communication with the first flow path at a second location that is downstream from the first location. The leak detection module, based on the first mass flow rate and the second mass flow rate, detects an error in at least one of a third mass flow rate of air entering the AOS device and a fourth mass flow rate of air exiting the AOS device.

In another aspect, the leak detection module detects an error in the at least one of the third and fourth mass flow rates based on: a first difference between the first mass flow rate and the second mass flow rate; and a second difference between the third mass flow rate and the fourth mass flow rate. In another aspect, the leak detection module detects an error in the at least one of the third and fourth mass flow rates when the first difference is greater than the second difference by a predetermined amount. In another aspect, the third mass flow rate and the fourth mass flow rate are predetermined. In another aspect, the AOS device includes a third flow meter that measures the third mass flow rate and a fourth flow meter that measures the fourth mass flow rate.

In other aspects, the exhaust gas sampling system further includes a second valve and a third valve. The second valve allows communication between the first flow path and the inlet of the AOS device when the second valve is open and prevents communication between the first flow path and the inlet of the AOS device when the second valve is closed. The third valve allows communication between the first flow path and the outlet of the AOS device when the third valve is open and prevents communication between the first flow path and the outlet of the AOS device when the third valve is closed. In another aspect, the leak detection module adjusts at least one of the third mass flow rate and the fourth mass flow rate based on measurements of the first mass flow rate and the second mass flow rate taken when the first valve, the second valve, and the third valve are closed.

A second example of exhaust gas sampling system according to the principles of the present disclosure includes a dilution air tunnel, a dilution air supply passage, a first flow meter, a sampling probe, a return passage, a first valve, a second flow meter, and a leak detection module. The dilution air supply passage supplies dilution air to the dilution air tunnel. The first flow meter measures a first mass flow rate of air flowing through the dilution air supply passage. The sampling probe provides exhaust gas to the dilution air tunnel. The return passage is in fluid communication with an outlet of the dilution air tunnel. The first valve controls exhaust gas flow from the sampling probe to the return passage. The second flow meter measures a second mass flow rate of air flowing through the return passage. The leak detection module detects a leak in the exhaust gas sampling system based on measurements of the first mass flow rate and the second mass flow rate taken when the first valve is closed.

In one aspect, the leak detection module detects a leak in the exhaust system when the first mass flow rate is greater than the second mass flow rate by a predetermined amount. In another aspect, the first valve is disposed in the sampling probe. In another aspect, the sampling probe has an outlet disposed upstream from the dilution air tunnel, and the first valve is disposed in the dilution air supply passage downstream from the outlet of the sampling probe.

In other aspects, the exhaust gas sampling system further includes a connection passage and a valve assembly. The connection passage has an inlet in communication with the dilution air supply passage at a first location upstream from the outlet of the sampling probe and having an outlet in communication with the return passage at a second location upstream from the second flow meter. The valve assembly controls the flow of air to the outlet of the sampling probe and controls the flow of air through the connection passage from the first location to the second location.

In another aspect, the valve assembly includes a second valve and a third valve. The second valve is disposed in the dilution air supply passage downstream from the first location and upstream from the outlet of the sampling probe. The third valve is disposed in the connection passage downstream from the first location and upstream from the second location.

In another aspect, the exhaust gas sampling system further includes a heat exchanger disposed in the dilution air supply passage downstream from the first location. In another aspect, the exhaust gas sampling system further includes a cyclonic separator disposed in the return passage upstream from the second location.

An example method for detecting a leak in an exhaust gas sampling system according to the principles of the present disclosure includes supplying dilution air to a dilution air tunnel through a dilution air supply passage and closing a first valve to prevent exhaust gas flow from a sampling probe to a return passage in fluid communication with an outlet of the dilution air tunnel. The method further includes measuring a first mass flow rate of air flowing through the dilution air supply passage when the first valve is closed, and measuring a second mass flow rate of air flowing through the return passage when the first valve is closed. The method further includes detecting a leak in the exhaust gas sampling system based on the first mass flow rate and the second mass flow rate.

In one aspect, the method further includes detecting a leak in the exhaust gas sampling system based on a difference between the first mass flow rate and the second mass flow rate. In another aspect, the method further includes detecting a leak in the exhaust gas sampling system when the difference between the first mass flow rate and the second mass flow rate is greater than a predetermined value.

In another aspect, the method further includes controlling a valve assembly to prevent air flow from the dilution air supply passage to the dilution air tunnel and to allow air flow through a connection passage from a first location in the dilution air supply passage that is upstream from the outlet of the sampling probe to a second location in the return passage that is upstream from a third location where the second mass flow rate is measured, and measuring the first and second mass flow rates. In another aspect, the method includes detecting an error in at least one of a third mass flow rate of air entering an add on sampling (AOS) device and a fourth mass flow rate of air exiting the AOS device based on the first and second mass flow rates.

In another aspect, the method includes detecting an error in the at least one of the third and fourth mass flow rates based on a first difference between the first and second mass flow rates and a second difference between the third and fourth mass flow rates. In another aspect, the method includes detecting an error in the at least one of the third and fourth mass flow rates when the first difference is greater than the second difference by a predetermined amount. In another aspect, the method includes adjusting at least one of the third and fourth mass flow rates based on the error detected.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

An exhaust gas sampling apparatus according to the present disclosure includes a dilution air tunnel, a dilution air supply passage that supplies dilution air to the dilution air tunnel, and a sampling probe that provides exhaust gas to the dilution air tunnel. The exhaust gas sampling apparatus also includes a return passage disposed on the outlet side of the dilution air tunnel, and a valve assembly that isolates the sampling probe from the remainder of the apparatus when the valve assembly is closed. The exhaust gas sampling apparatus further includes a first flow meter disposed in the dilution air supply passage, and a second flow meter disposed in the return passage.

A system and method according to the present disclosure detects a leak in the exhaust gas sampling apparatus based on first and second mass flow rates measured by the first and second flow meter, respectively, when the valve assembly is closed. Since the first and second mass flow rates are measured when the valve assembly is closed, only dilution air is allowed to flow past both the first and second flow meters. The system and method then detects a leak in the exhaust gas sampling apparatus based on a difference between the first and second mass flow rates. Detecting a leak in the exhaust gas sampling apparatus in this way may be quicker and more accurate than conventional systems and methods for detecting a leak in an exhaust gas sampling apparatus.

Figure 1:
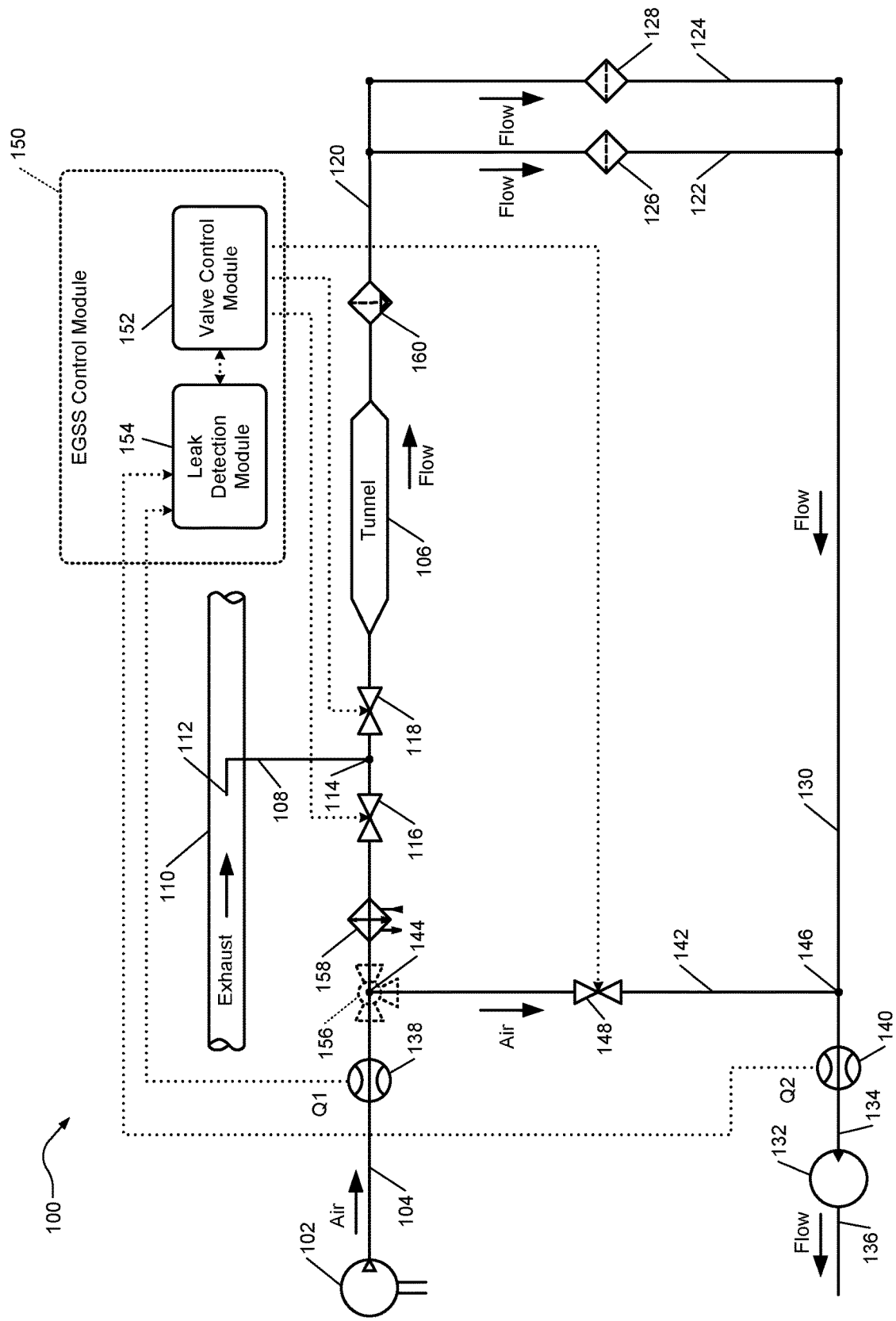
FIG. 1 is a schematic of a first example of an exhaust gas sampling system according to the principles of the present disclosure.

Referring to FIG. 1, an exhaust gas sampling system 100 includes a dilution air source, such as a compressor 102, a dilution supply passage 104, and/or a compressed air line in a building (not shown), which provides dilution air to a dilution air tunnel 106. The exhaust gas sampling system 100 further includes a sampling probe 108 that provides exhaust gas flowing through a tailpipe 110 to the dilution air tunnel 106. The sampling probe 108 has an inlet 112 that is disposed in the tailpipe 110 and an outlet 114 that may be disposed in the dilution air supply passage 104 upstream from the dilution air tunnel 106 as shown. Alternatively, the outlet 114 of the sampling probe 108 may be disposed in the dilution air tunnel 106.

A first valve 116 is disposed in the dilution air supply passage 104 and regulates the flow of dilution air to the outlet 114 of the sampling probe 108. A second valve 118 is disposed in the dilution air supply passage 104 and regulates the flow of dilution air and/or exhaust gas from the sampling probe 108 to the dilution air tunnel 106. The first and second valves 116 and 118 may be electromechanical valves and are adjustable to a fully open position, a fully closed position, and, in various implementations, to a plurality of positions between the fully open and closed positions.

The first valve 116 prevents dilution air from flowing past the outlet 114 of the sampling probe 108 when the first valve 116 is closed. The first valve 116 allows dilution air to flow past the outlet 114 of the sampling probe 108 when the first valve 116 is open. The second valve 118 prevents exhaust gas flow from the outlet 114 of the sampling probe 108 to the dilution air tunnel 106 when the second valve 118 is closed. The second valve 118 allows exhaust gas flow from the outlet 114 of the sampling probe 108 to the dilution air tunnel 106 when the second valve 118 is open.

A delivery passage 120 delivers dilution air and/or exhaust gas from the dilution air tunnel 106 to a first filter passage 122 and a second filter passage 124. A first particulate filter 126 and a second particulate filter 128 are disposed in the first filter passage 122 and the second filter passage 124, respectively. Although two particulate filters are shown, the exhaust gas sampling system 100 may include a larger number of particulate filters (e.g., three) or a smaller number of particulate filters (e.g., one).

A return passage 130 receives exhaust gas flow and/or dilution air flow from the first and second filter passages 122 and 124. The return passage 130 is in fluid communication with an outlet side of the dilution air tunnel 106 via the delivery passage 120 and the first and second filter passages 122 and 124. The return passage 130 may deliver exhaust gas flow and/or dilution air flow to an emissions reduction device before the flow is released into the atmosphere.

A pump 132 is disposed in the return passage 130 to create a vacuum on an inlet side 134 of the pump 132. The vacuum created by the pump 132 draws the exhaust gas flow and/or the dilution air flow from the inlet side 134 of the pump 132 to an outlet side 136 of the pump 132. The pump 132 may be a venturi pump and may utilize flow from the dilution air source to create the vacuum.

A first flow meter 138 measures a first mass flow rate Q1 of dilution air in the dilution air supply passage 104. The first flow meter 138 is disposed in the dilution air supply passage 104 upstream from the outlet 114 of the sampling probe 108, as shown. A second flow meter 140 measures a second mass flow rate Q2 of dilution air and/or exhaust gas in the return passage 130. The second flow meter 140 is disposed in the return passage 130 upstream from the pump 132.

A connection passage 142 connects the dilution air supply passage 104 to the return passage 130. The connection passage 142 has an inlet 144 and an outlet 146. The inlet 144 of the connection passage 142 is in fluid communication with the dilution air supply passage 104 at a first location that is downstream from the first flow meter 138 and upstream from the outlet 114 of the sampling probe 108. The outlet 146 of the connection passage 142 is in fluid communication with the return passage 130 at a second location that is upstream from the second flow meter 140.

A third valve 148 is disposed in the connection passage 142 and regulates the flow of dilution air from the dilution air supply passage 104 to the return passage 130 through the connection passage 142. The third valve 148 may be an electromechanical valve and is adjustable to a fully open position, a fully closed position, and, in various implementations, to a plurality of positions between the fully open and closed positions. The third valve 148 allows flow from the dilution air supply passage 104 to the return passage 130 through the connection passage 142 when the third valve 148 is open. The third valve 148 prevents flow from the dilution air supply passage 104 to the return passage 130 through the connection passage 142 when the third valve 148 is closed.

An exhaust gas sampling system (EGSS) control module 150 receives signals from various sensors in the exhaust gas sampling system 100 and controls various components of the exhaust gas sampling system 100 based on the signals received. The EGSS control module 150 includes a valve control module 152 and a leak detection module 154. The valve control module 152 controls the positions of the first valve 116, the second valve 118, and the third valve 148. The leak detection module 154 detects a leak in the exhaust gas sampling system 100.

During a leak test, the valve control module 152 may close the first valve 116 and open the third valve 148 to divert dilution air flow from the dilution air supply passage 104 to the return passage 130 via the connection passage 142. In addition, the valve control module 152 may close the first and second valves 116 and 118 to isolate the sampling probe 108 within the portion of the dilution air supply passage 104 extending between the first and second valves 118. Adjusting the first, second, and third valves 116, 118, and 148 in this way ensures that only dilution air flows past the first and second flow meters 138 and 140. In turn, the leak detection module 154 may detect a leak in the exhaust gas sampling system 100 based on a difference between the first mass flow rate Q1 and the second mass flow rate Q2.

The leak detection module 154 may detect a leak in a first flow path and/or a second flow path based on the difference between the first mass flow rate Q1 and the second mass flow rate Q2. The first flow path extends through the dilution air supply passage 104, the dilution air tunnel 106, the delivery passage 120, the filter passages 122 and 124, and the return passage 130. The second flow path extends through the connection passage 142.

In various implementations, the first valve 116 and the third valve 148 may be replaced with a single three-way valve 156. The first valve 116, the second valve 118, the third valve 148, and/or the three-way valve 156 may be referred to as a valve assembly. In implementations where the first and third valves 148 are replaced with the three-way valve 156, the valve control module 152 controls the positions of the second valve 118 and the three-way valve 156.

The exhaust gas sampling system 100 may further include a heat exchanger 158 and a cyclonic separator 160. The heat exchanger 158 heats and/or cools dilution air flowing through the dilution air supply passage 104. The heat exchanger 158 may be a Peltier-based heat exchanger. The cyclonic separator 160 is a particle separator that allows smaller particles to pass therethrough while trapping larger particles. For example only, the smaller particles may be approximately 1 micrometer in diameter, while the larger particles may be approximately 10 micrometers in diameter.

Figure 2:
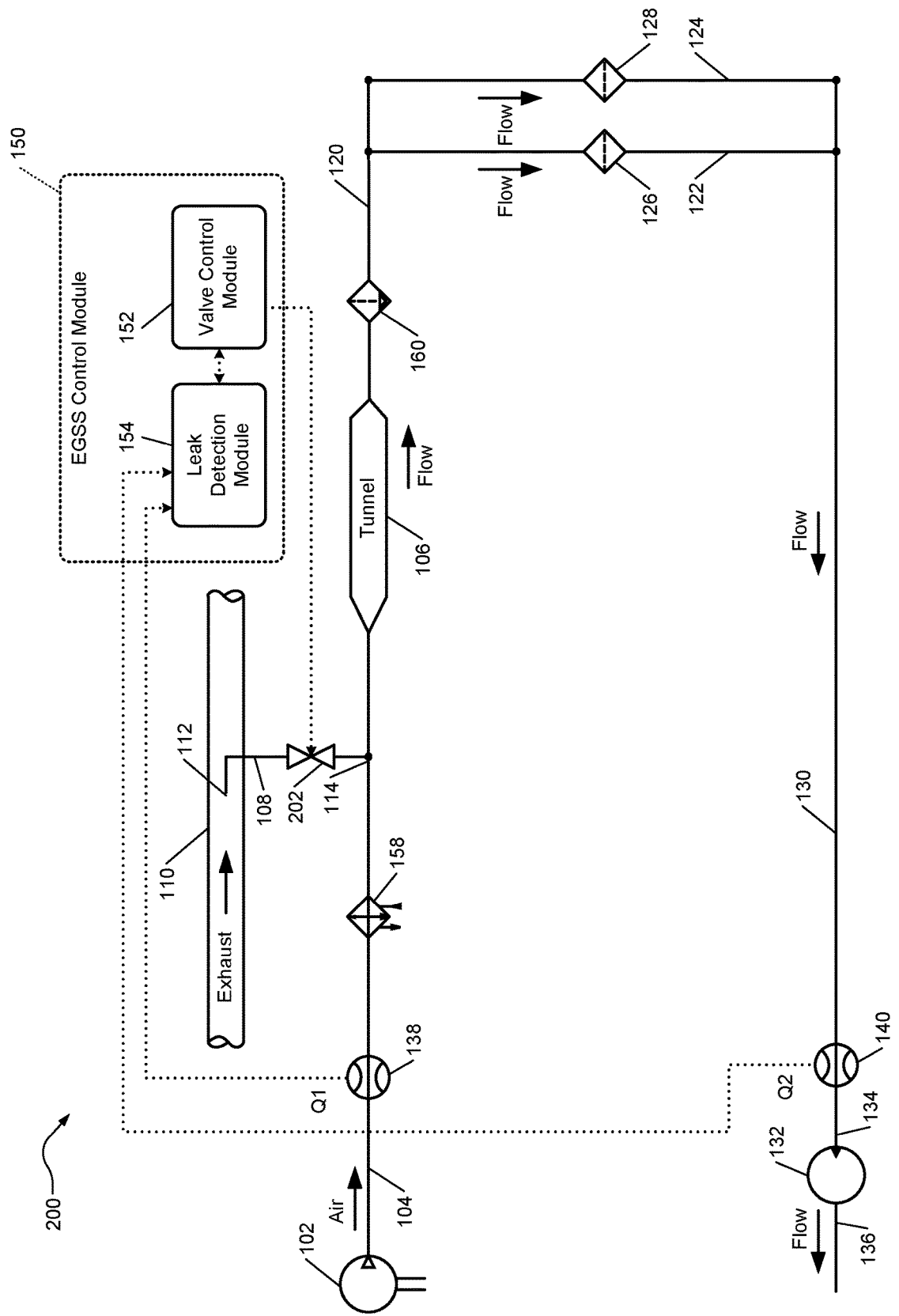
FIG. 2 is a schematic of a second example of an exhaust gas sampling system according to the principles of the present disclosure.

FIG. 2 illustrates an exhaust gas sampling system 200 that is similar to the exhaust gas sampling system 100 of FIG. 1. However, in the exhaust gas sampling system 100 of FIG. 1, the first and second valves 116 and 118 are disposed in the dilution air supply passage 104 and are closed to isolate the sampling probe 108 as described above. In contrast, in the exhaust gas sampling system 200 of FIG. 2, the first and second valves 116 and 118 are omitted, and a single valve 202 is disposed in the sampling probe 108 and is closed to isolate the sampling probe 108 from the entire first flow path. In turn, dilution air is allowed to flow through the entire first flow path without mixing with exhaust gas from the sampling probe 108. As a result, the connection passage 142 may be omitted.

The valve 202 prevents exhaust gas flow to the dilution air supply passage 104 and the dilution air tunnel 106 when the valve 202 is closed. The valve 202 allows exhaust gas flow to the dilution air supply passage 104 and the dilution air tunnel 106 when the valve 202 is open. The valve 202 may be an electromechanical valve and is adjustable to a fully open position, a fully closed position, and, in various implementations, to a plurality of positions between the fully open and closed positions.

Figure 3:
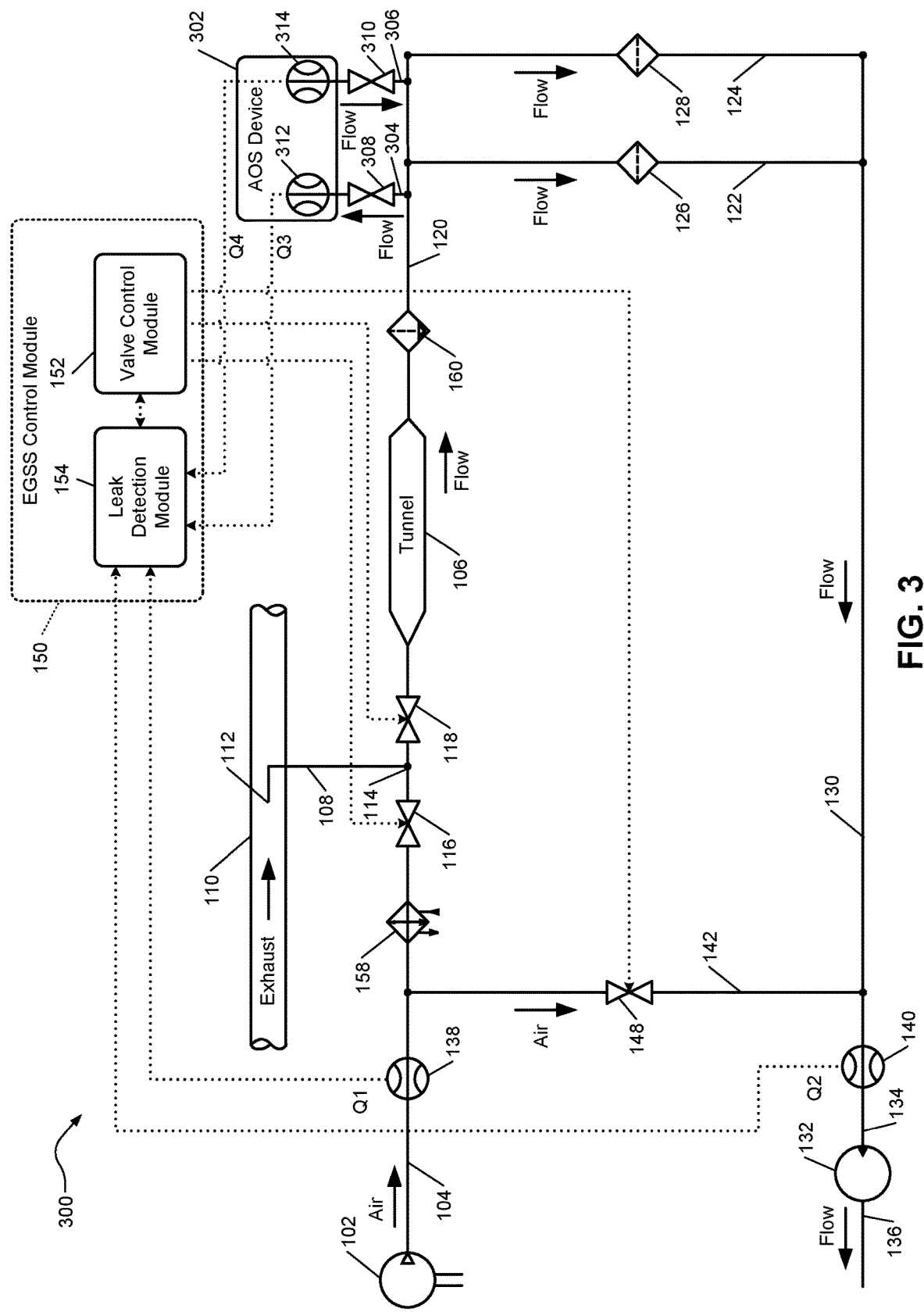
FIG. 3 is a schematic of a third example of an exhaust gas sampling system according to the principles of the present disclosure.

FIG. 3 illustrates an exhaust gas sampling system 300 that is also similar to the exhaust gas sampling system 100 of FIG. 1. However, the exhaust gas sampling system 300 further includes an add on sampling (AOS) device 302. The AOS device 302 detects properties of particles in exhaust gas flowing through the first flow path and allows gas to escape the first flow path.

The AOS device 302 may measure particle count and/or particle size. In one example, the AOS device 302 may measure particle count via a batch test in which particles are collected over a predetermined period and then counted at the end of the predetermined period. In another example, the AOS device 302 may provide an instantaneous reading of particle count indicating transient changes in particle count.

Exhaust gas and dilution air enters the AOS device 302 through an inlet passage 304 and exits the AOS device 302 through an outlet passage 306. An inlet valve 308 is disposed in the inlet passage 304 and regulates flow through the inlet passage 304. An outlet valve 310 is disposed in the outlet passage 306 and regulates flow through the outlet passage 306. The inlet and outlet valves 308 and 310 may be electromechanical valves and are adjustable to a fully open position, a fully closed position, and, in various implementations, to a plurality of positions between the fully open and closed positions.

The AOS device 302 includes a third flow meter 312 and a fourth flow meter 314. The third flow meter 312 measures a third mass flow rate Q3 of air flowing through the inlet passage 304. The fourth flow meter 314 measures a fourth mass flow rate Q4 of air flowing through the outlet passage 306.

Figure 4:
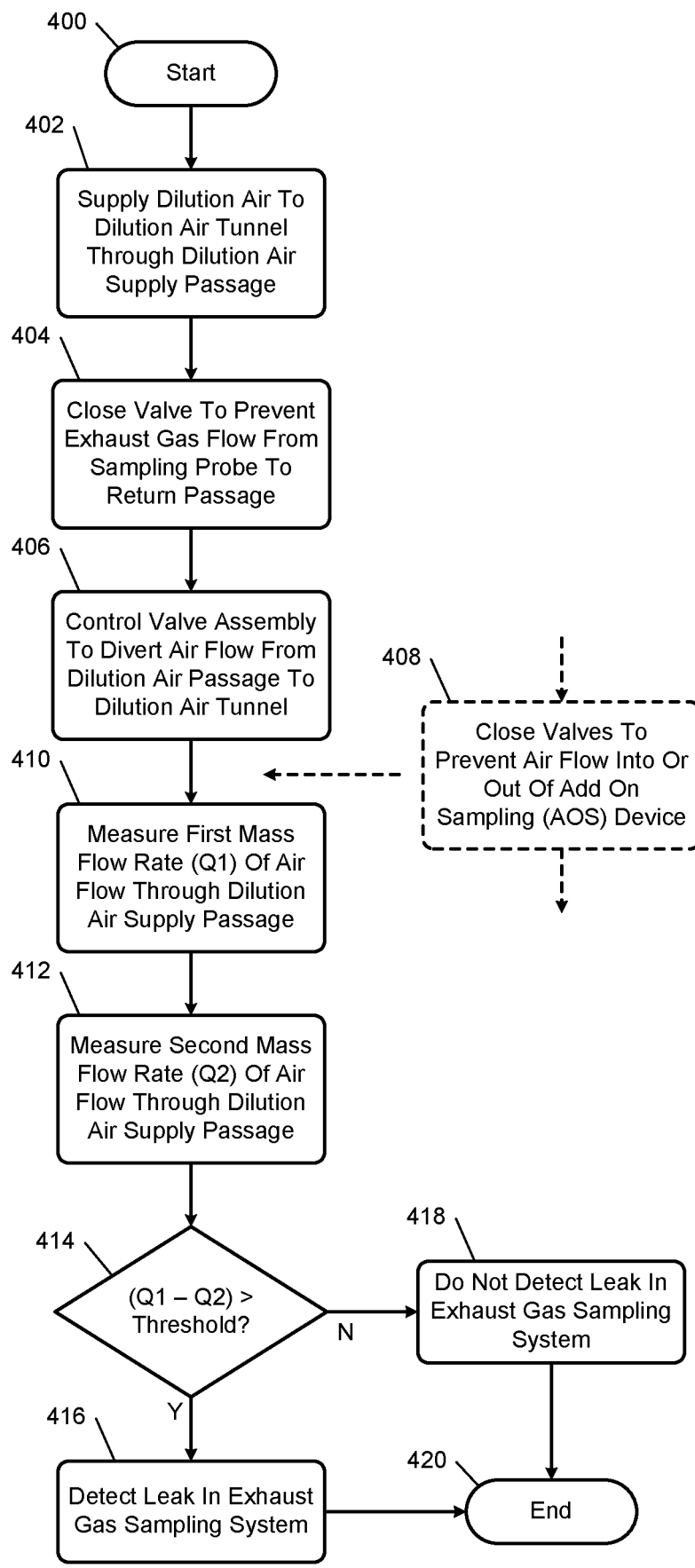
FIG. 4 is a flowchart illustrating an example method for detecting a leak in an exhaust gas sampling system according to the principles of the present disclosure.

Referring to FIG. 4, a method for detecting a leak in an exhaust gas sampling system such as the exhaust gas sampling systems 100, 200, or 300 begins at step 400. The method is described in the context of the valve control module 152 and the leak detection module 154 of FIG. 1. However, the particular modules that perform the steps of the method may be different than the description below and/or the method may be implemented apart from the modules of FIG. 1. For example, the method may be implemented by one module or by more than two modules.

At step 402, the method supplies dilution air to the dilution air tunnel 106 through the dilution air supply passage 104. At step 404, the valve control module 152 closes the second valve 118 (FIGS. 1 and 3) or the valve 202 (FIG. 2) to prevent exhaust gas flow from the sampling probe 108 to the dilution air tunnel 106. At step 406, the valve control module 152 controls a valve assembly, including the first valve 116 and the third valve 148, to divert air flow from the dilution air supply passage 104 to the dilution air tunnel 106 through the connection passage 142 (FIGS. 1 and 3). Step 406 may be omitted when diagnosing a leak in the exhaust gas sampling system 200 of FIG. 2.

When detecting a leak in an exhaust gas sampling system such as the exhaust gas sampling system 300 of FIG. 3, the method may perform step 408. In step 408, the valve control module 152 closes the inlet and outlet valves 308 and 310 to prevent air flow into or out of the AOS device 302. At step 410, the first flow meter 138 measures the first mass flow rate Q1 of air flow through the dilution air supply passage 104. At step 412, the second flow meter 140 measures the first mass flow rate Q2 of air flow through the return passage 130.

At step 414, the leak detection module 154 determines whether a difference between the first and second flow rates Q1 and Q2 is greater than a threshold (e.g., a predetermined value between 0 grams per second (g/s) and 0.02 g/s). If the difference between the first and second flow rates Q1 and Q2 is greater than the threshold, the leak detection module 154 continues at step 416 and detects a leak in the exhaust gas sampling system. Otherwise, the leak detection module 154 continues at step 418 and does not detect a leak in the exhaust gas sampling system.

When detecting a leak in the exhaust gas sampling system 300 of FIG. 3, the leak detection module 154 may adjust the first value based on the third and fourth mass flow rates Q3 and Q4 to account for the amount of dilution air that escapes the system 300 through the AOS device 302. For example, the leak detection module 154 may increase the first value by an amount that is equal to the third mass flow rate Q3 minus the fourth mass flow rate Q4. The method ends at step 420.

Figure 5:
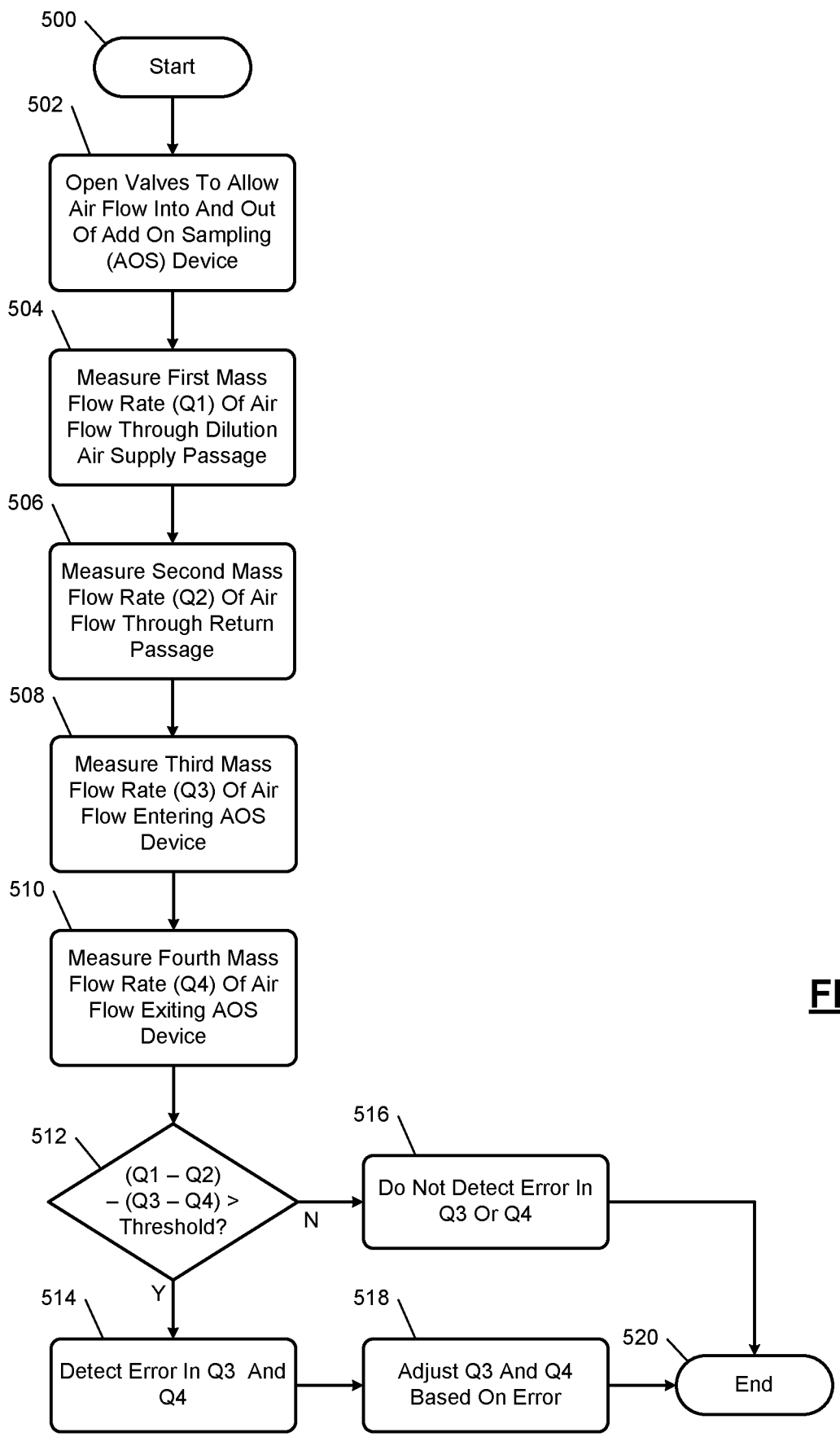
FIG. 5 is a flowchart illustrating an example method for detecting an error in a mass flow rate measurement according to the principles of the present disclosure.

Referring to FIG. 5, a method for detecting an error in the third and fourth mass flow rates Q3 and Q4 of FIG. 3 begins at step 500. The method is described in the context of the valve control module 152 and the leak detection module 154 of FIG. 1. However, the particular modules that perform the steps of the method may be different than the description below and/or the method may be implemented apart from the modules of FIG. 1. For example, the method may be implemented by one module or by more than two modules. In another example, while the leak detection module 154 is described as detecting an error in the third and fourth mass flow rates Q3 and Q4 and adjusting these mass flow rates based on the error detected, these functions may be performed by an error detection module and an adjustment module, respectively.

The method detects an error in the third and fourth mass flow rates Q3 and Q4 based on a difference between the first and second mass flow rates Q1 and Q2. Thus, the method may be performed after performing the method of FIG. 4 to determine how much of this difference, if any, is due to a leak in the exhaust gas sampling system. In addition, while the method of FIG. 5 is performed, the valve control module 152 may keep the first and second valves 116 and 118 closed and keep the third valve 148 open.

At step 502, the valve control module 152 opens the inlet and outlet valves 308 and 310 to allow air flow into and out of the AOS device 302. At step 504, the first flow meter 138 measures the first mass flow rate Q1 of air flow through the dilution air supply passage 104. At step 506, the second flow meter 140 measures the second mass flow rate Q2 of air flow through the return passage 130. At step 508, the third flow meter 312 measures the third flow rate Q3 entering the AOS device 302. At step 510, the fourth flow meter 314 measures the fourth flow rate Q4 exiting the AOS device 302. In various implementations, instead of measuring the third and fourth mass flow rates Q3 and Q4, the third and fourth mass flow rates Q3 and Q4 may be predetermined and stored in the leak detection module 154.

At step 512, the leak detection module 154 determines a first difference between the first and second flow rates Q1 and Q2 (e.g., Q1-Q2) and determines a second difference between the third and fourth mass flow rates Q3 and Q4 (e.g., Q3-Q4). The leak detection module 154 then determines whether a third difference between the first difference (e.g., Q1-Q2) and the second difference (e.g., Q3-Q4) is greater than a threshold (e.g., a predetermined value between 0 g/s and 0.02 g/s). If the third difference is greater than the threshold, the leak detection module 154 continues at step 514 and detects an error in the third and fourth mass flow rates Q3 and Q4. Otherwise, the leak detection module 154 continues at step 516 and does not detect an error in the third mass flow rate Q3 or the fourth mass flow rate Q4.

At step 518, the leak detection module 154 adjusts the third and fourth mass flow rates Q3 and Q4 based on the error detected in the third and fourth mass flow rates Q3 and Q4. In one example, the leak detection module 154 adjusts the third mass flow rate Q3 and/or the fourth mass flow rate Q4 such that the third difference between the first difference (e.g., Q1-Q2) and the second difference (e.g., Q3-Q4) is within the threshold. Additionally or alternatively, the leak detection module 154 may adjust the second difference between the third and fourth mass flow rates Q3 and Q4 based on the error detected in the third and fourth mass flow rates Q3 and Q4. For example, the leak detection module 154 may adjust the second difference (e.g., Q3-Q4) by an amount equal to the amount by which the third difference is greater than the threshold. The method ends at step 520.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

What is claimed is:

1. An exhaust gas sampling system comprising:
   a dilution air source that provides dilution air to a first flow path;
   a first flow meter that measures a first mass flow rate of air in the first flow path;
   a sampling probe that has an outlet disposed in the first flow path downstream from the first flow meter and that provides exhaust gas to the first flow path;
   a second flow meter that measures a second mass flow rate of air in the first flow path downstream from the sampling probe;
   a first valve that allows exhaust gas flow from the sampling probe to the second flow meter when the first valve is open and that prevents exhaust gas flow from the sampling probe to the second flow meter when the first valve is closed;
   a leak detection circuit that detects a leak in the exhaust gas sampling system based on measurements of the first mass flow rate and the second mass flow rate taken when the first valve is closed; and
   an add on sampling (AOS) device that detects properties of particles in exhaust gas flowing through the first flow path and that allows gas to escape the first flow path, wherein:
   the AOS device has an inlet in communication with the first flow path at a first location that is downstream from the outlet of the sampling probe;
   the AOS device has an outlet in communication with the first flow path at a second location that is downstream from the first location; and
   the leak detection circuit, based on the first mass flow rate and the second mass flow rate, detects an error in at least one of a third mass flow rate of air entering the AOS device and a fourth mass flow rate of air exiting the AOS device.

2. The exhaust gas sampling system of claim 1 wherein the leak detection circuit detects an error in the at least one of the third and fourth mass flow rates based on:
   a first difference between the first mass flow rate and the second mass flow rate; and
   a second difference between the third mass flow rate and the fourth mass flow rate.

3. The exhaust gas sampling system of claim 2 wherein the leak detection circuit detects an error in the at least one of the third and fourth mass flow rates when the first difference is greater than the second difference by a predetermined amount.

4. The exhaust gas sampling system of claim 1 wherein the third mass flow rate and the fourth mass flow rate are predetermined.

5. The exhaust gas sampling system of claim 1 wherein the AOS device includes a third flow meter that measures the third mass flow rate and a fourth flow meter that measures the fourth mass flow rate.

6. The exhaust gas sampling system of claim 1 further comprising:
   a second valve that allows communication between the first flow path and the inlet of the AOS device when the second valve is open and that prevents communication between the first flow path and the inlet of the AOS device when the second valve is closed; and
   a third valve that allows communication between the first flow path and the outlet of the AOS device when the third valve is open and that prevents communication between the first flow path and the outlet of the AOS device when the third valve is closed.

7. The exhaust gas sampling system of claim 6 wherein the leak detection circuit adjusts at least one of the third mass flow rate and the fourth mass flow rate based on measurements of the first mass flow rate and the second mass flow rate taken when the first valve, the second valve, and the third valve are closed.

8. An exhaust gas sampling system comprising:
a dilution air tunnel;
a dilution air supply passage that supplies dilution air to the dilution air tunnel;
a first flow meter that measures a first mass flow rate of air flowing through the dilution air supply passage;
a sampling probe that provides exhaust gas to the dilution air tunnel;
a return passage in fluid communication with an outlet of the dilution air tunnel;
a first valve that controls exhaust gas flow from the sampling probe to the return passage;
a second flow meter that measures a second mass flow rate of air flowing through the return passage; and
a leak detection circuit that detects a leak in the exhaust gas sampling system based on measurements of the first mass flow rate and the second mass flow rate taken when the first valve is closed, wherein the sampling probe has an outlet disposed in the dilution air supply passage upstream from the dilution air tunnel, and the first valve is disposed in the dilution air supply passage downstream from the outlet of the sampling probe and upstream from the dilution air tunnel.

9. The exhaust gas sampling system of claim 8 further comprising:
a connection passage having an inlet in communication with the dilution air supply passage at a first location upstream from the outlet of the sampling probe and having an outlet in communication with the return passage at a second location upstream from the second flow meter; and
a valve assembly that controls the flow of air to the outlet of the sampling probe and that controls the flow of air through the connection passage from the first location to the second location.

10. The exhaust gas sampling system of claim 9 wherein:
the valve assembly includes a second valve and a third valve;
the second valve is disposed in the dilution air supply passage downstream from the first location and upstream from the outlet of the sampling probe; and
the third valve is disposed in the connection passage downstream from the first location and upstream from the second location.

11. The exhaust gas sampling system of claim 9 further comprising a heat exchanger disposed in the dilution air supply passage downstream from the first location.

12. The exhaust gas sampling system of claim 9 further comprising a cyclonic separator disposed in the return passage upstream from the second location.

13. A method for detecting a leak in an exhaust gas sampling system, the method comprising:
supplying dilution air to a dilution air tunnel through a dilution air supply passage;
closing a first valve to prevent exhaust gas flow from a sampling probe to a return passage in fluid communication with an outlet of the dilution air tunnel;
measuring a first mass flow rate of air flowing through the dilution air supply passage when the first valve is closed;
measuring a second mass flow rate of air flowing through the return passage when the first valve is closed;
detecting a leak in the exhaust gas sampling system based on the first mass flow rate and the second mass flow rate; and
based on the first and second mass flow rates, detecting an error in at least one of a third mass flow rate of air entering an add on sampling (AOS) device and a fourth mass flow rate of air exiting the AOS device.

14. The method of claim 13 further comprising detecting an error in the at least one of the third and fourth mass flow rates based on a first difference between the first and second mass flow rates and a second difference between the third and fourth mass flow rates.

15. The method of claim 14 further comprising detecting an error in the at least one of the third and fourth mass flow rates when the first difference is greater than the second difference by a predetermined amount.

16. The method of claim 15 further comprising adjusting at least one of the third and fourth mass flow rates based on the error detected.

* * * * *